United States Patent [19]

Hotvet

[11] Patent Number: 5,550,923
[45] Date of Patent: Aug. 27, 1996

US005550923A

[54] DIRECTIONAL EAR DEVICE WITH ADAPTIVE BANDWIDTH AND GAIN CONTROL

[75] Inventor: David A. Hotvet, Savage, Minn.

[73] Assignee: Minnesota Mining and Manufacturing Company, St. Paul, Minn.

[21] Appl. No.: 300,345

[22] Filed: Sep. 2, 1994

[51] Int. Cl.$^6$ .................................................. H03G 5/00
[52] U.S. Cl. ............................ 381/72; 381/94; 381/103
[58] Field of Search .............................. 381/72, 158, 25, 381/155, 71, 94, 104, 106, 107, 68.2, 68.4, 68, 103

[56] References Cited

U.S. PATENT DOCUMENTS

| | | |
|---|---|---|
| 3,306,991 | 2/1967 | Wood . |
| 3,394,226 | 7/1968 | Andrews, Jr. . |
| 3,573,400 | 4/1971 | Sessler et al. ........................... 381/155 |
| 3,678,416 | 7/1972 | Burwen ..................................... 381/94 |
| 3,952,158 | 4/1976 | Kyle et al. . |
| 4,061,875 | 12/1977 | Freifeld et al. ........................... 381/72 |
| 4,119,814 | 10/1978 | Harless . |
| 4,490,585 | 12/1984 | Tanaka . |
| 4,701,953 | 10/1987 | White . |
| 4,718,099 | 1/1988 | Hotvet . |
| 4,750,207 | 6/1988 | Gebert et al. . |
| 4,789,044 | 12/1988 | Akino . |
| 4,790,018 | 12/1988 | Preves et al. . |
| 4,904,078 | 2/1990 | Gorike . |
| 4,928,311 | 5/1990 | Trompler . |
| 4,969,534 | 11/1990 | Kolpe et al. . |
| 5,027,410 | 6/1991 | Williamson et al. ................... 381/68.4 |
| 5,070,527 | 12/1991 | Lynn ........................................ 381/72 |
| 5,214,709 | 5/1993 | Ribic ..................................... 381/68.1 |
| 5,216,711 | 6/1993 | Takagi et al. ........................... 379/433 |
| 5,257,420 | 11/1993 | Byrne, Jr. . |
| 5,355,418 | 10/1994 | Kelsey et al. ............................. 381/72 |
| 5,402,498 | 3/1995 | Waller, Jr. ............................... 381/106 |

FOREIGN PATENT DOCUMENTS

| | | | |
|---|---|---|---|
| 2460535 | 6/1976 | Germany .......................... A61F 11/02 |
| WO93/20669 | 10/1993 | WIPO .............................. H04R 25/00 |
| WO93/21876 | 11/1993 | WIPO . |
| WO94/27525 | 12/1994 | WIPO . |

OTHER PUBLICATIONS

Carlson et al., "Subminiature Directional Microphones", *Journal of the Audio Engineering Society*, Sep. 10, 1973, pp. 305–309.

Markus, John; *Guidebook of Electronic Circuits;* Chapter 33, "Filter Circuits–Active"; 1974; pp. 252–264.

*Primary Examiner*—Curtis Kuntz
*Assistant Examiner*—Ping W. Lee
*Attorney, Agent, or Firm*—Gary L. Griswold; Walter N. Kirn; Kari H. Bartingale

[57] ABSTRACT

An ear device protects a user from damaging sound levels while permitting the user to hear and understand conversation in a noisy environment. The device includes an enclosure system for at least partially isolating the user's ear drums from ambient sounds, at least on directional microphone, an adaptive band pass filter and a speaker. The adaptive band pass filter further includes adaptive high pass and adaptive low pass filters which adaptively and independently control the range of the pass band depending upon the characteristics of the noise in the user's environment. A speaker transmits the processed signal to the user. The adaptive filter also includes a detector connected to receive the processed signal which controls the gain of the system to prevent overcompression of the audio signal. The adaptive filter further includes an adaptive compression circuit utilizing multiple time constants to control the response time of the adaptive filter under various conditions.

13 Claims, 9 Drawing Sheets

NOISE

VOICE ALARM

DIRECTIONAL EAR DEVICE WITH ADAPTIVE BANDWIDTH AND GAIN CONTROL

FIELD OF THE INVENTION

The disclosure concerns electronic hearing protection devices that protect the user from excessive or damaging levels of sound, and is specifically concerned with the need of the user to hear and understand conversation or other communications in a noisy environment.

BACKGROUND

The human ear is very sensitive to damage by high levels of noise, including damage caused by high amplitude bursts of noise, and by long term exposure to high levels of noise. Various devices for protecting the ear from excessive levels of sound have therefore been developed. However, in addition to requiring ear protection in a noisy environment, a user often must be able to hear and understand certain sounds, such as conversation, warning sirens or other communication, while in the noisy environment. Such a situation can arise in a factory or other environment with high and potentially damaging levels of background noise.

To address this situation, various devices have utilized signal processing techniques in attempts to suppress unwanted noise while still allowing the user to hear desired sounds. These techniques have included low pass filtering or a combination of low and high pass filtering, as well as attenuation of large amplitude audio signals. However, these techniques often attenuate or filter out frequencies important to the communication desired to be heard. In addition, devices that clip or reject some frequencies of the human voice can distort sound quality, and the result can be acoustically unpleasant and interfere with understanding.

SUMMARY

To overcome the drawbacks in the art described above, and to overcome other problems which will become apparent upon reading and understanding the present specification, the directional ear device described herein protects a user from excessive sound levels while allowing the user to hear and understand conversation in a noisy environment.

The present ear device includes an enclosure system for at least partially isolating a user's eardrums from background noise, at least one directional microphone, an adaptive filter and a speaker. In use, the directional microphone is pointed in the direction from which the desired sounds emanate, such as toward a person with whom the user is conversing. Sounds picked up by the directional microphone are processed by the adaptive filter. The adaptive filter compensates for varying levels of background noise by adaptively adjusting the low and high cutoff frequencies of the pass band, and by adaptively adjusting the amount of gain of the signal. Thus, the audio signal is processed in a way such that hearing and understanding of human speech or other communication are optimized. The device thus protects the user from damaging levels of sound while maintaining optimal sound quality regardless for the particular level of background noise in the user's environment.

BRIEF DESCRIPTION OF THE DRAWINGS

The various objects, features and advantages of the present ear device will be understood upon reading and understanding the following Detailed Description, in which.

Each of FIGS. 10–13 show block diagrams of alternate embodiments of the present ear device.

DETAILED DESCRIPTION

Figure 1A:
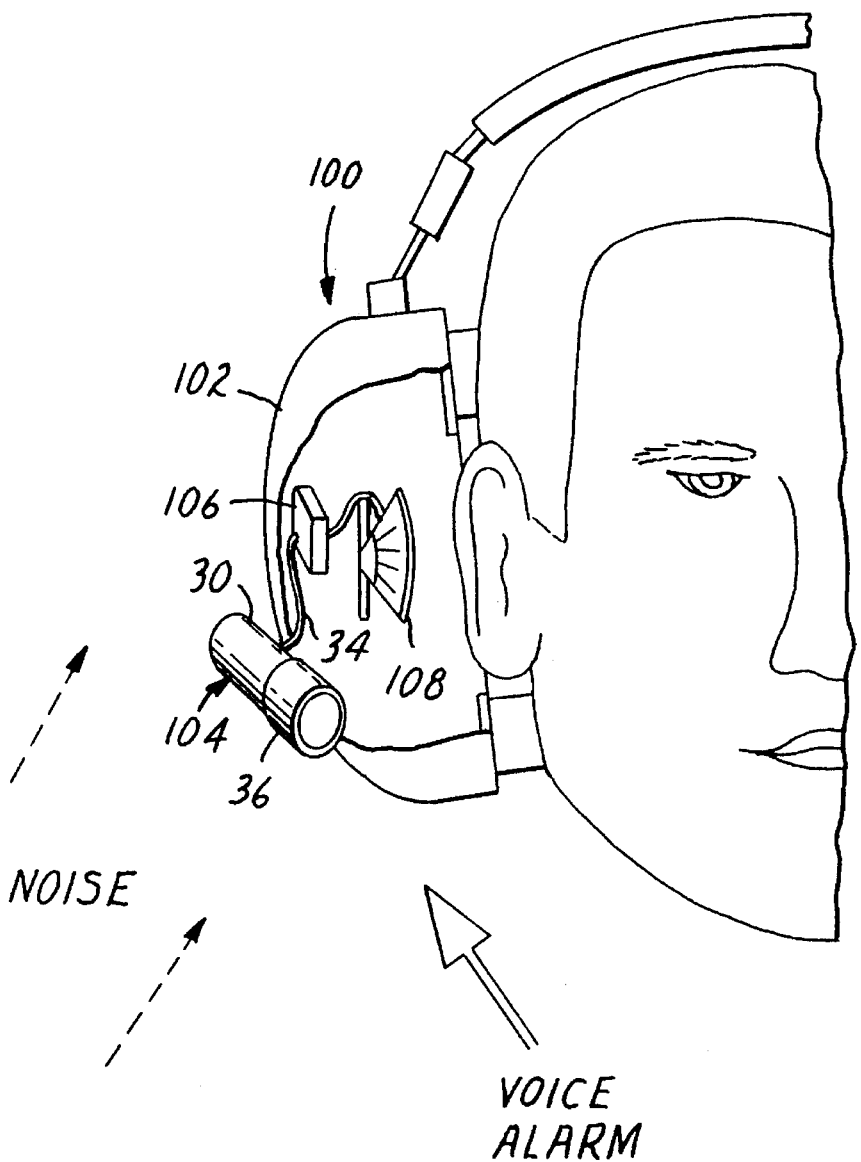
FIG. 1A shows a simplified illustration of the present ear device.
Figure 1B:
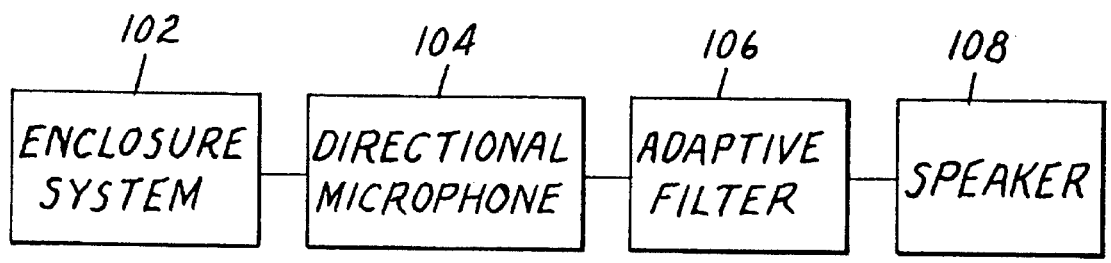
FIG. 1B shows a simplified block diagram of the present ear device.

FIG. 1B shows a simplified block diagram of the present ear device 100. Ear device 100 includes an enclosure system 102, directional microphone 104, adaptive filter 106 and a speaker 108. As described in more detail below, enclosure system 102 can include protective ear muffs, earpiece, a hood or other ear protective device which at least partially isolates a user from damaging sound levels. Preferably the enclosure means provides a high degree of isolation, e.g., such as 20 to 30 dB. However, it shall be understood that any degree of isolation, whether greater than or less than 20 to 30 dB, may be appropriate for a given application.

The preferred ear device 100 shown in FIG. 1A also includes at least one directional microphone 104. The use of a directional microphone 104 in the present ear device 100 provides several advantages. First, being directional, microphone 104 only picks up sounds originating from a certain range about the direction in which the microphone is pointed. This greatly eliminates much of the noise which may be present in the user's environment, as such noise often emanates from many directions at once.

The degree of directionality of the directional microphone 104 is preferably adjustable so that unwanted noise can be reduced to a level necessary to protect the user from damaging sound levels and to filter out sounds that inhibit speech intelligibility. Ideally, noises are attenuated by the directionality of the microphone only to the extent necessary to accomplish those purposes, thus allowing the user to hear a variety of sounds such as warning calls or sounds that may come from various directions.

The directional microphone 104 is also preferably adjustable by the user to permit the microphone to be pointed in any direction. In a typical situation, the directional microphone is pointed in the direction faced by the user toward a person with whom they are conversing. In another situation, a firefighter might wish to hear persons only directly to the rear, while noises created by a fire to the front are being attenuated. In other situations, it may be desirable to employ two directional microphones, one pointed forwardly and the other rearwardly. In other situations, the user may need to hear voices coming from the side rather than from the front or rear. The ability to adjust the direction in which the microphone is pointed allows the user to adapt the present ear device to the changing nature of such conditions.

In some other applications, however, it may be desirable to permit adjustments to the present ear device to be made only by a qualified industrial hygienist to guard against accidental injury to the wearer's hearing.

Figure 2:
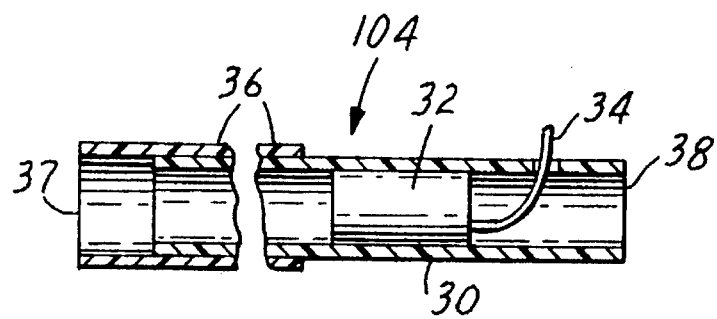
FIG. 2 shows the preferred directional microphone.

FIG. 2 shows a preferred directional microphone 104. The directional microphone 104 has a cylindrical housing 30 in which is mounted a directional microphone cartridge 32 having wire leads 34 by which the cartridge 32 is connected to the adaptive filter 106. Telescopically mounted on the housing 30 is a shroud 36 which adjusts the degree of directionality of the microphone by changing the spacing between the front port 37 and the rear port 38. In the preferred embodiment, the string length (defined as the external distance from one radius beyond the center point of front port 37 following the outside surface of shroud 36 and housing 30 to one radius beyond the center point of rear port 38) of the directional microphone 104 is adjustable between 32 and 47 mm.

Figure 3B:
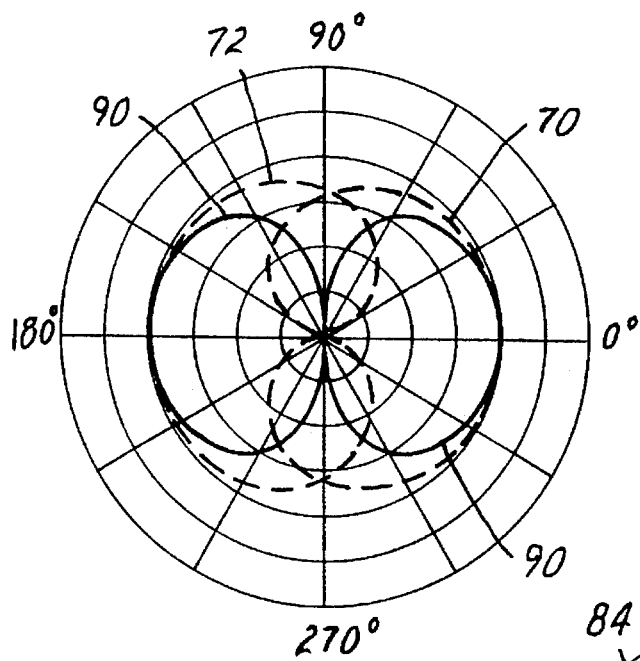
FIGS. 3A and 3B are polar graphs showing the directional characteristics of the present ear device.
Figure 3A:
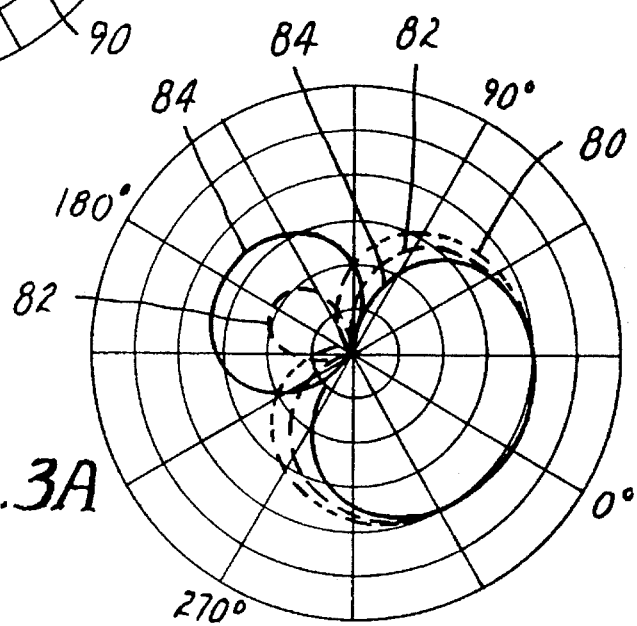

FIG. 3A shows log polar response patterns produced by adjustment of the shroud 36 of the preferred directional microphone 104 shown in FIG. 2. Cardioid patterns 80, 82 and 84 show the response of the preferred directional microphone 104 as it is adjusted from lower to higher degrees of directionality. The cardioid pattern 80 shows the response of the directional microphone 104 when adjusted for the lowest degree of directionality, e.g., with the shroud 36 positioned for the shortest string length. The cardioid pattern 82 shows the response when the shroud 36 is adjusted to achieve greater rejection at 90°. This is achieved by moving the shroud 36 outwardly from the shortest string length position. The cardioid pattern 84 shows a response when the shroud is adjusted to the longest string length. In this case, the result is greater rejection at 110°.

FIG. 3B shows the log polar response patterns of a microphone system employing two directional microphones where the microphones are pointed in opposite directions. The cardioid patterns 70 and 72 are response patterns produced by each of the two microphones when they are pointed in opposite directions, respectively. The pattern 90 is produced by subtracting the signals 70 and 72 of the two directional microphones from each other. The cardioid patterns 70 and 72 represent what may be the lowest degree of directionality at which either of the two directional microphones can be adjusted while affording noise protection, while the combined response pattern represents the highest degree of directionality at 90° that can be obtained.

Referring again to FIG. 1A, the ear device 100 further preferably includes an adaptive filter 106, having low pass and high pass filters which are independently controlled. Preferably, the low pass gain and frequency cutoff are controlled by the amplitude of high frequency noises. Likewise, the high pass gain and frequency cutoff are controlled by the amplitude of low frequency noises. In a quiet environment, the adaptive filter 106 passes a wide band of frequencies so that transmitted speech possesses a natural sound quality. In progressively noisier environments, the adaptive filter 106 passes progressively narrower bands of frequencies such that only those frequencies of the human voice that are vital to speech intelligibility or other desired communication are allowed to pass in very noisy environments.

The ear device 100 also includes a speaker 108, which receives the processed electrical signals from the adaptive filter 106, and converts them to an audible signal for ultimate transmission to the user.

Figure 4:
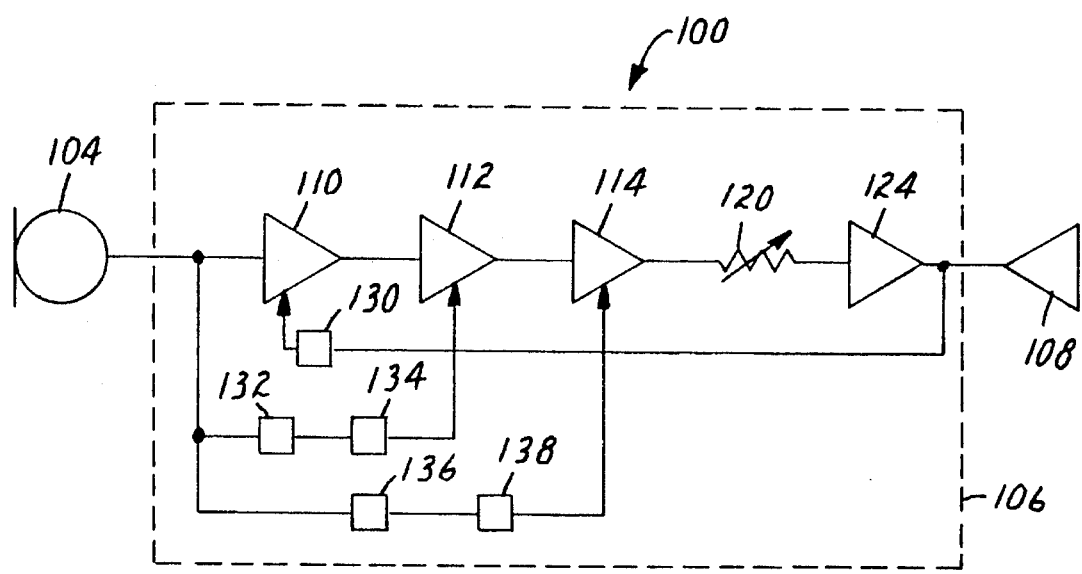
FIG. 4 is a detailed block diagram of the adaptive filter of the ear device of FIG. 1.

FIG. 4 shows a block diagram of adaptive filter 106. The adaptive filter preferably performs the signal processing tasks of adaptively adjusting the gain of the filter to compensate for varying levels of background noise, and of independently controlling low and high pass cutoffs in response to varying levels of background noise. The adaptive filter 106 equalizes signals produced by the directional microphone 104 to afford a substantially flat response over the range of frequencies needed to provide a natural sounding reproduction of aural signals such as the human voice. This ensures that the frequency range of the human voice is sufficiently amplified in a quiet environment and that noises within that range are not amplified past the upper limit of safe hearing in a noisy environment. Preferably the adaptive filter 106 equalizes frequencies between 300 and 3000 Hz.

To accomplish the equalization of frequencies, adaptive filter 106 preferably includes an automatic gain control (AGC) limiter 110 that electronically adjusts the level of the signal received from directional microphone 104 to protect the user from damaging signal levels in very noisy environments, while providing a certain amount of gain to desired signals if needed in a quiet environment. Detector 130 senses the varying AC level on the output of power amplifier 124 and converts it to a varying DC level to control the response of the AGC limiter 110. The user is thus protected from damaging sound levels in very noisy environments, while maintaining sufficient gain in quiet environments. In addition, detector 130, by virtue of sensing the output of power amp 124, prevents over compression of the incoming audio signal which would occur if detector 130 instead sensed the output of high or low pass filter 112 and 114.

Experimentation with the present ear protector has shown that when incoming frequencies below 1000 Hz and/or above 2500 Hz are excluded, the human voice sounds unnatural to the user in a quiet environment. To compensate for this effect, the adaptive filter 106 preferably senses the noisiness of the environment to control the range of the pass band. As a result, a larger pass band provides a natural sound equality in a quiet environment, and a narrower pass band affords the dual function of ear protection and communication in noisy environments.

To accomplish the adaptive response to varying levels of background noise, the adaptive filter 106 includes an adaptive high pass filter 112 and an adaptive low pass filter 114 that together with coupled feedforward loops provide an adaptive bandpass filter. The adaptive high pass feedforward loop includes a low pass filter 132 and a cutoff control 134, while the adaptive low pass feedforward loop includes a high pass filter 136 and a cutoff control 138. The output from the adaptive low pass filter 114 is fed into a user adjustable volume control 120, and a power amplifier 124. The processed signal is then acoustically sent to the user via speaker 108.

The frequency cutoff of both the adaptive low and high pass filters 112 and 114 are independently and adaptively controlled. The cutoff frequency of the adaptive high pass filter 112, as determined by cutoff control 134, is controlled by the amplitude of low frequency sounds which are sensed by the low pass filter 132. Similarly, the cutoff frequency of the adaptive low pass filter 114, as determined by cutoff control 138, is controlled by the amplitude of high frequency sounds which are sensed by high pass filter 136.

In operation, the low pass filter 132 senses the AC amplitude of low frequency sounds (e.g., frequencies below 500 Hz in the preferred embodiment). This AC amplitude is then used to control the cutoff frequency of the adaptive high pass filter 112 as determined by cutoff control 134. Similarly, high pass filter 136 senses the AC amplitude of high frequency sounds (e.g., frequencies above 2 kHz in the preferred embodiment). This AC amplitude is then used to control the cutoff frequency of the adaptive low pass filter 114.

When the amplitude of the incoming signal is very high (i.e., very noisy) low pass filter 132 and cutoff control 134 operate to increase the cutoff frequency of high pass filter 112, thus narrowing the range of the pass band on the low frequency side. When the amplitude of the incoming signal is not as high, low pass filter 132 and cutoff control 134 operate to decrease the cutoff frequency of high pass filter 112 to allow a wider range of frequencies to pass in the less noisy environment. Similarly, high pass filter 136 and low frequency cutoff control 138 operate to decrease the cutoff frequency of low pass filter 114 when input signal levels are high and increase the cutoff frequency when input signal levels are low. Thus, only frequencies most vital to speech intelligibility are passed to the user in very noisy environments, while a broader passband is allowed in quieter environments for enhanced sound quality.

Figure 5:
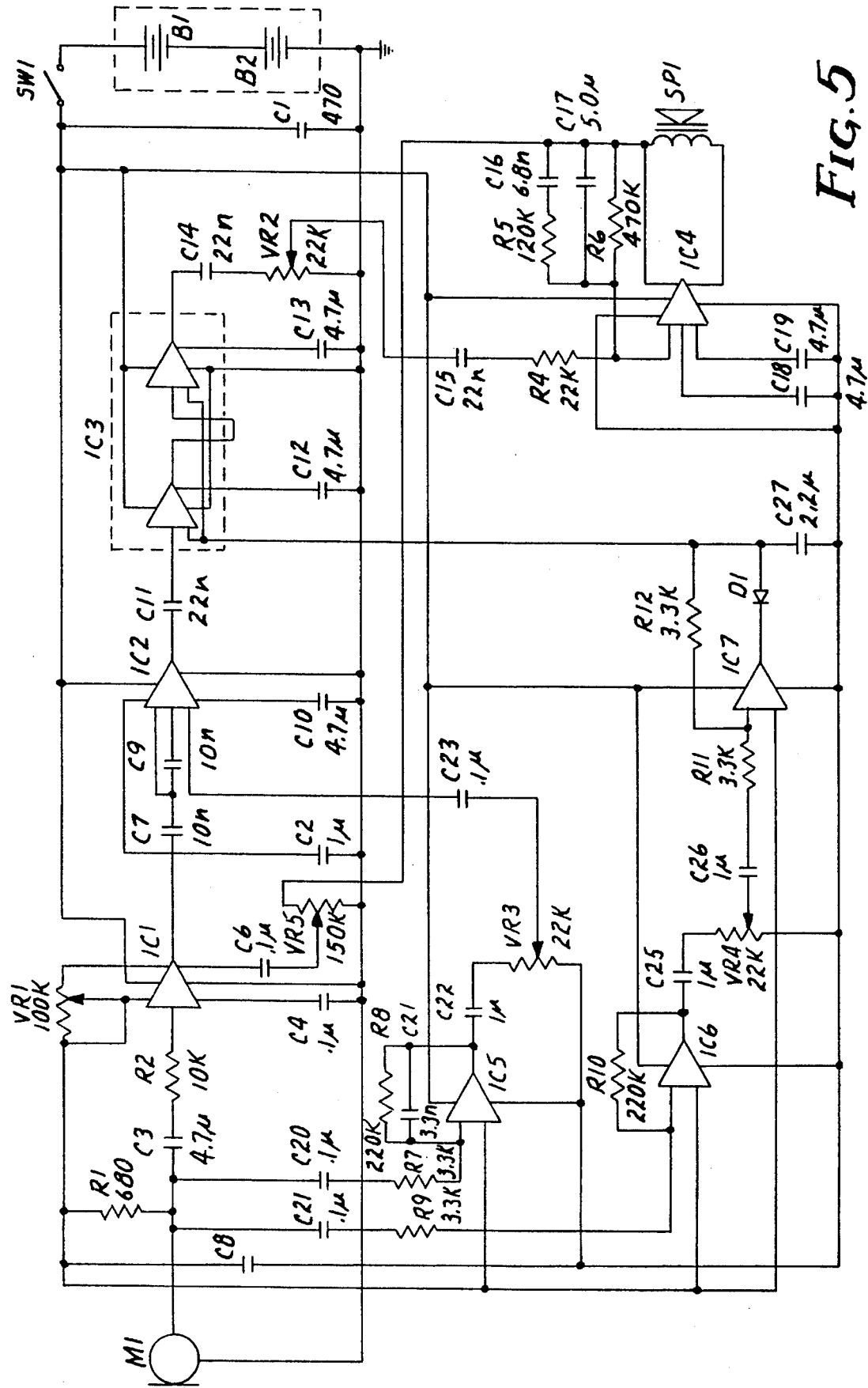
FIG. 5 is an electrical schematic diagram of the adaptive filter of FIG. 1.

FIG. 5 shows an electrical schematic diagram of the adaptive filter 106 shown in block diagram form in FIG. 1B. In FIG. 5, IC1 and associated discrete components comprise the automatic gain control (AGC) limiter 110 and detector 130 that equalize the audio signal from the directional microphone. The output of IC1 is fed to an adaptive high pass filter IC2, the feedforward loop of which includes low pass filter IC5 and a variable resistor VR3 which, in combination with C22, forms cutoff control 134. The output from the adaptive high pass filter IC2 is fed into adaptive low pass filter IC3, the feedforward loop of which includes high pass filter IC3 and variable resistor VR4 which, in combination with C25, forms cutoff control 138. The output of adaptive low pass filter IC6 is connected to power amplifier IC4 through a user adjustable volume control VR2. Power amplifier IC4 and associated discrete components provide a flat response over the desired frequency range.

Figure 6A:
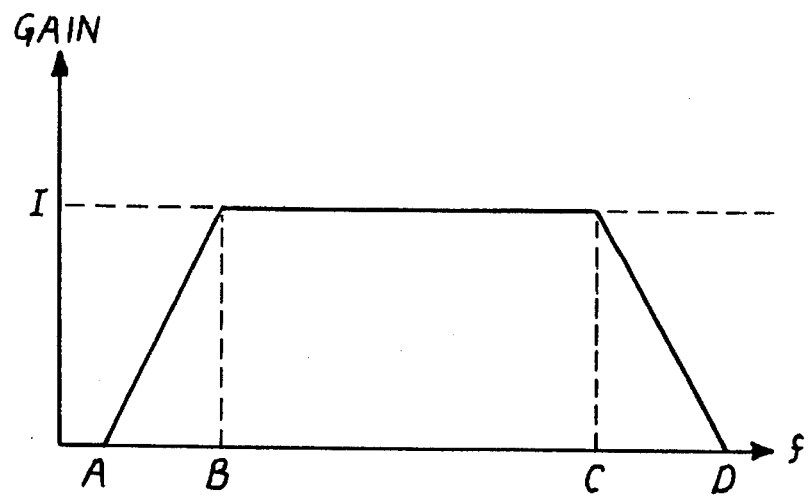
FIGS. 6A, 6B and 6C show simplified frequency response curves of the present adaptive filter.
Figure 6B:
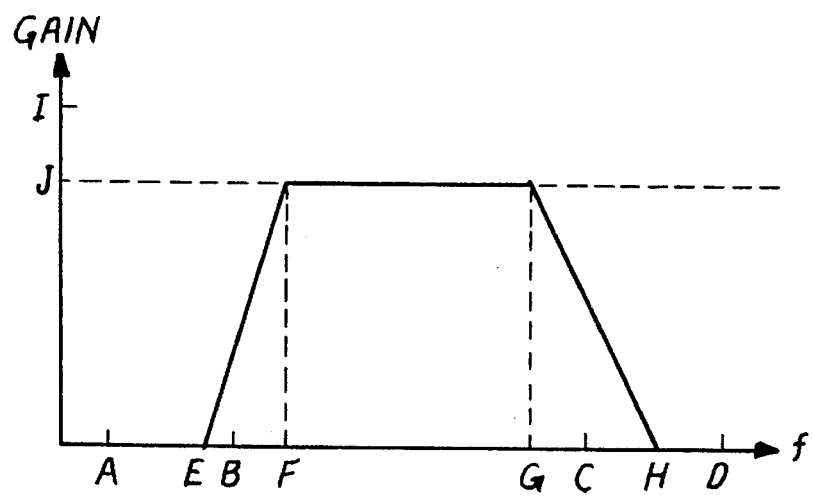
Figure 6C:
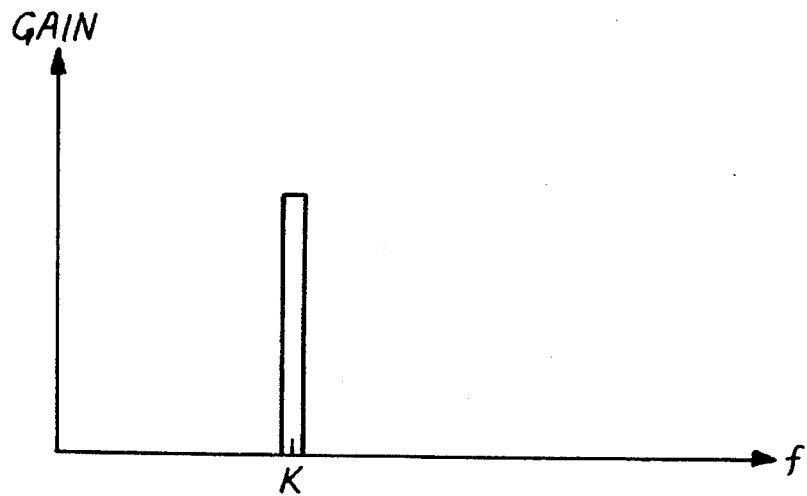

FIGS. 6A–6C show exemplary frequency response curves of the adaptive filter shown in FIGS. 4 and 5. FIG. 6A shows a response curve of the present adaptive filter in a quiet environment. The response curve of FIG. 6A is produced by combining the response from the adaptive high pass filter and the adaptive low pass filter to produce a band pass filter. The adaptive high pass filter passes a band of high frequencies above the cutoff frequency B and substantially attenuates frequencies below the cutoff. The slope or roll-off of the adaptive high pass filter is preferably at least 20 dB per decade. Similarly, the adaptive low pass filter substantially passes a band of frequencies below the cutoff frequency C, and attenuates those above the cutoff frequency. The slope or roll-off of the low pass filter is preferably at least 20 dB per decade. The gain I of the adaptive filter is indicated on the vertical axis.

In response to progressively higher levels of noise, the present ear device adaptively adjusts the gain of the adaptive filter, and either the low frequency cutoff, the high frequency cutoff, or both, depending on the noise, to produce a progressively narrower pass bind. The slope of the response curve for both the adaptive low and high pass filters can also be adjusted. This adaptive filtering accomplishes the dual function of affording sufficient ear protection to the user in noisy environments while passing frequencies important for speech intelligibility or other desired communication. FIG. 6B shows a frequency response curve of the present adaptive filter in an environment having more high and low frequency noise than that of FIG. 6A. In FIG. 6B, the high pass cutoff frequency has been increased from B in FIG. 6A to F in FIG. 6B, while the low pass cutoff frequency has been decreased from C in FIG. 6A to G in FIG. 6B. In addition, the gain of the adaptive filter has decreased from I in FIG. 6A to J in FIG. 6B to further compress the larger amplitude (louder) signal.

In environments having large amplitude low frequency noise, but no high frequency noise, or vice versa, only the respective low or high cutoff frequency would be adjusted, thus maintaining the broadest possible pass band and providing the optimum sound quality available in that particular environment.

The limiting case is shown in FIG. 6C. There the pass band has been reduced to allow passage of only a single frequency, K. This limiting case may be used where the user's environment is so loud that speech communication may be impossible, but where it is necessary for the user to at least be able to hear other forms of communication such as warning alarms or sirens. In that instance, the single frequency K could be set to match that of the warning siren or bell, thus allowing the user to hear this important and potentially life saving communication while still affording protection from the noise in the environment. This single frequency may be amplified to the upper limit of safe hearing for special danger.

In the preferred embodiment, high pass cutoff control VR3 allows the cutoff frequency of the adaptive high pass filter to be adjusted within the frequency range 300 to 1000 Hz. Similarly, low pass cutoff control VR4 allows the low pass cutoff frequency to be adjusted within the frequency range 10K to 3K Hz.

In the preferred embodiment, AGC IC1 and compression threshold VR5 and associated discrete components limit the acoustic output of the ear protector at a level not to exceed 85 dB.

Figure 7:
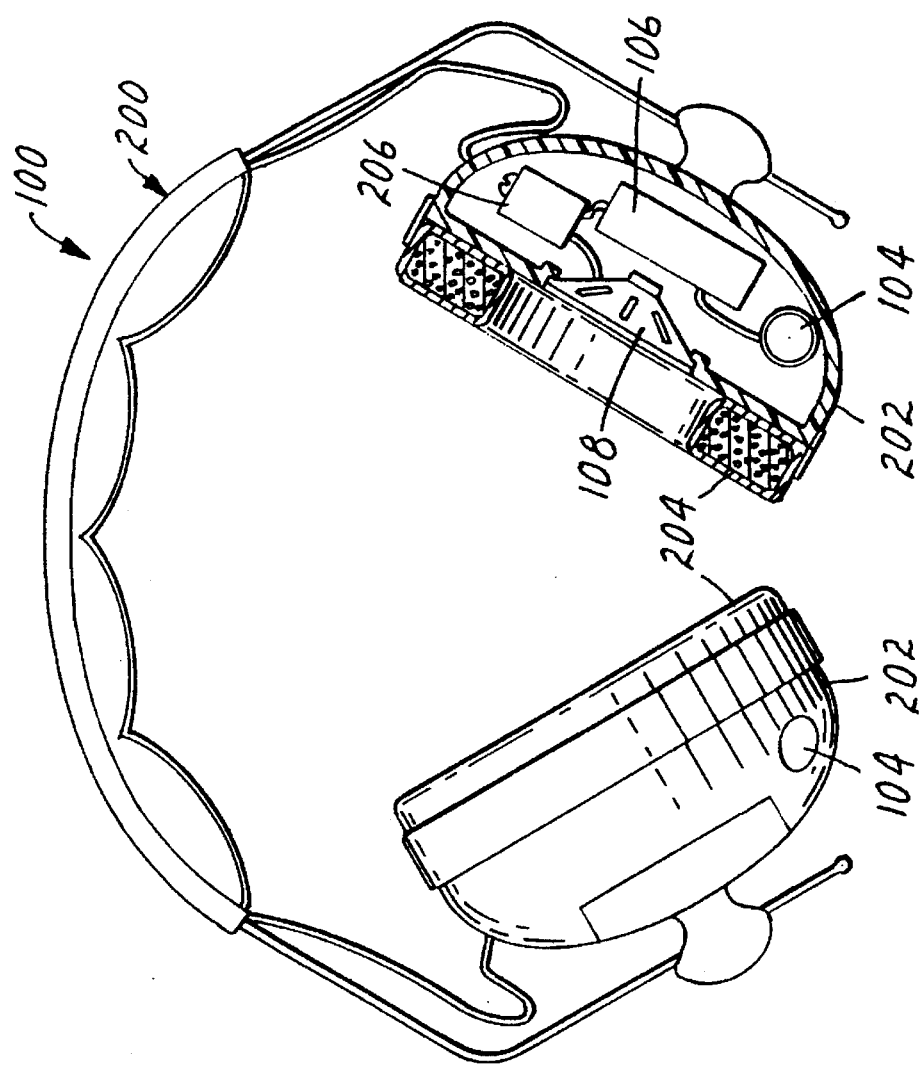
FIG. 7 shows the present ear device where the enclosure system is ear protective earmuffs.
Figure 8:
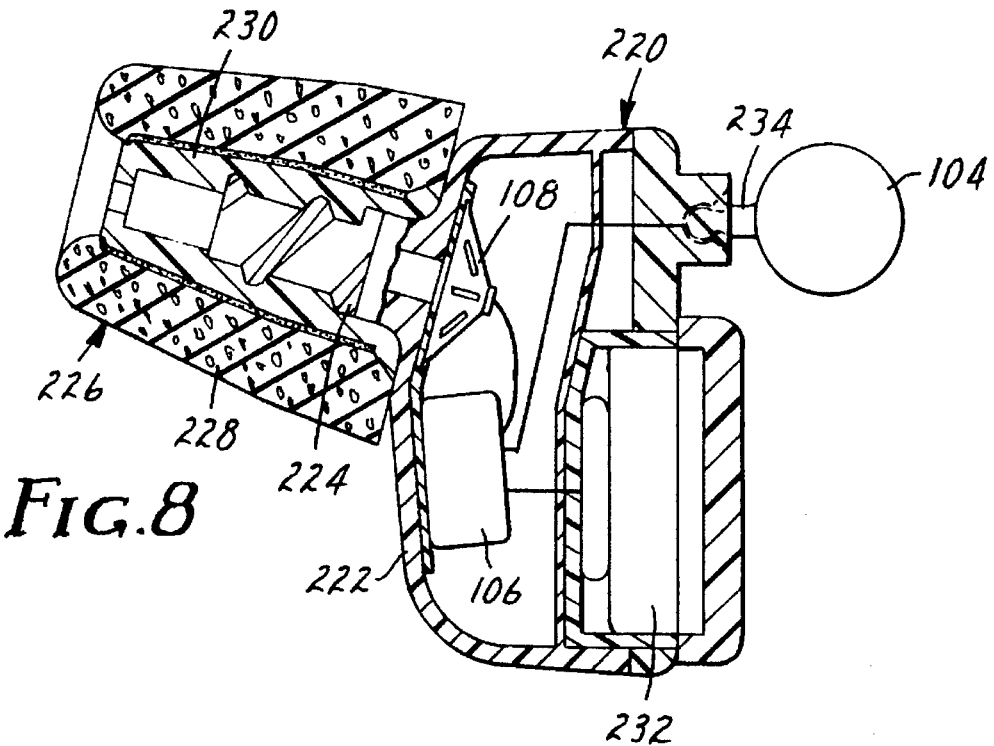
FIG. 8 shows the present ear device where the enclosure system is an earpiece.
Figure 9:
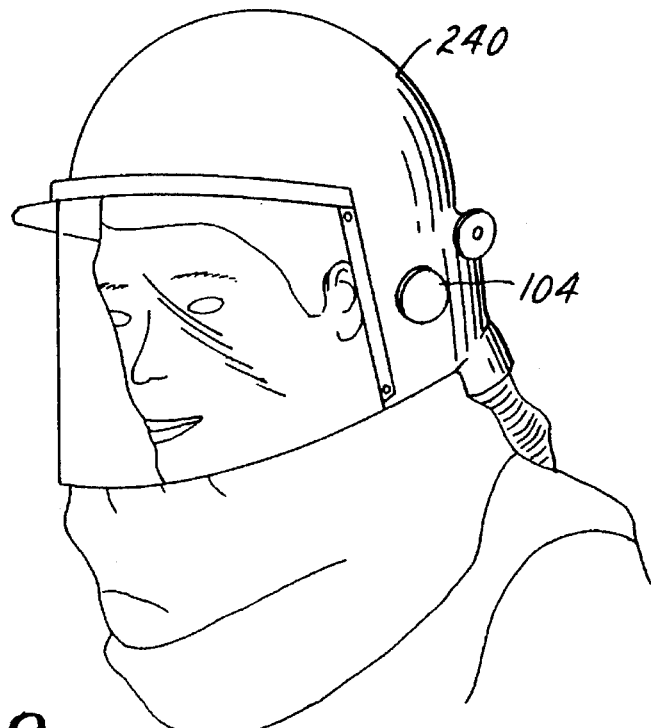
FIG. 9 shows the present ear device where the enclosure system is a hood.

As described above with respect to FIG. 1, the enclosure system 102 of the present ear device can take any of several forms. FIGS. 7–9 show exemplary embodiments of the enclosure system 102. FIG. 7 shows an embodiment of the present ear device 100 in which the enclosure system includes ear protecting earmuffs 200. Earmuffs 200 include a pair of earpieces 202, each equipped with an ear seal 204, a directional microphone 104, a power supply 206, an adaptive filter 106 and a speaker 108.

FIG. 8 shows an embodiment of the present ear device in which the enclosure system 102 is formed of an ear protecting earplug 220 which is constructed in a manner similar to the in-the-ear hearing aid shown in FIG. 1 of coassigned U.S. Pat. No. 4,969,534 (Kolpe et al.). Ear plug 220 has a molded plastic casing 222 from which a screw thread 224 projects. A user-disposable sleeve 226 consists of retarded recovery foam 228 mounted on a flexible, elongated plastic duct 230. When the sleeve 226 is threaded onto the screw thread 224, the foam 228 comes to rest against the casing 222 as shown. Mounted within the casing 222 are speaker 108, adaptive filter 106, and a power source 232. A directional microphone 104 is mounted on the external surface of the casing by a universal joint 234 that permits a user to adjust the direction in which the microphone is pointed.

FIG. 9 shows an embodiment of the present ear device in which the enclosure system is formed of a hood 240. Mounted on the exterior of the hood is a directional microphone 104, and mounted within the hood adjacent each of the wearer's ears are adaptive filter 106 and a speaker 108 (not shown), each of which is connected to the microphone 104 in the manner described herein.

Figure 10:
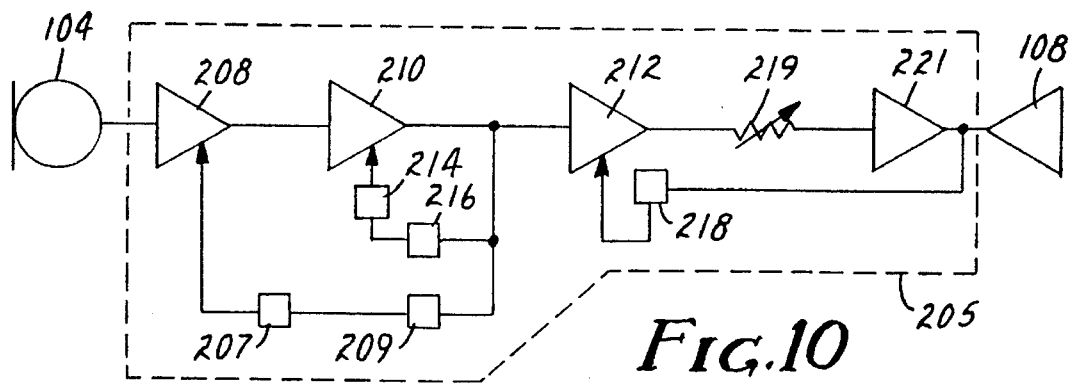

The present ear device described thus far and as specifically shown in FIGS. 4 and 5 can take a number of other forms. FIGS. 10–13 show alternate embodiments of the adaptive filter of the present ear device. It shall be understood, however, that other structural changes could also be made without departing from the spirit and scope of the present invention. In the circuitry of FIG. 10, adaptive filter 205 includes an adaptive high pass filter 208 and an adaptive low pass filter 210 that together with coupled feedback loops provide an adaptive band pass filter. Feedback control of the adaptive high pass filter 208 consists of a low pass filter 209 and cutoff control 207, and feedback control of the adaptive low pass filter 210 is provided by a high pass filter 216 and an cutoff control 214. Output of the adaptive bandpass filter is fed into an AGC limiter 212, which is controlled by detector 218 which is connected to the output of the power amplifier 221.

Figure 11:
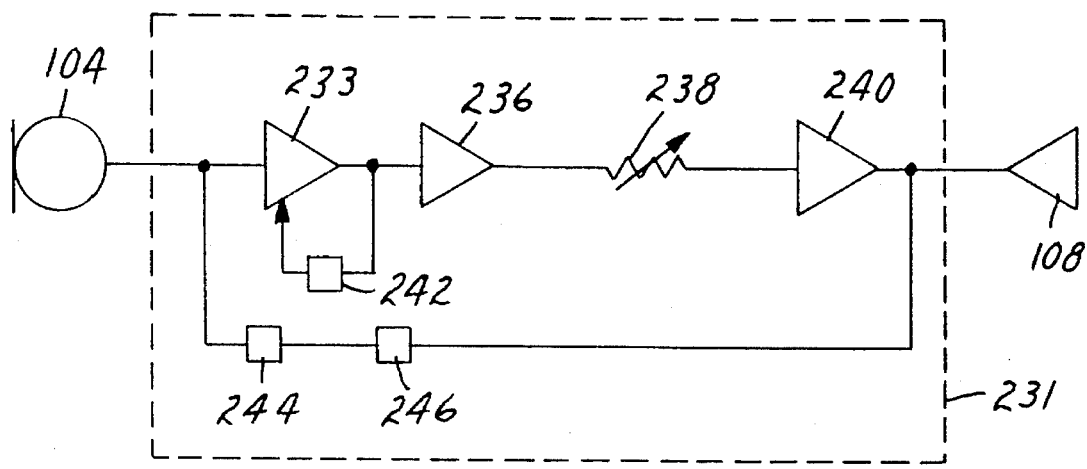

The circuit of FIG. 11 shows the adaptive high pass filter portion of the circuit of FIG. 4. It shall be understood that the adaptive low pass portion of the circuit of FIG. 4 could also be used alone. In FIG. 11, adaptive filter 231 includes AGC limiter 233, controlled by detector 242, and adaptive high pass filter 236 which is controlled by the feedforward loop including low pass filter 244 and cutoff control 246.

Figure 12:
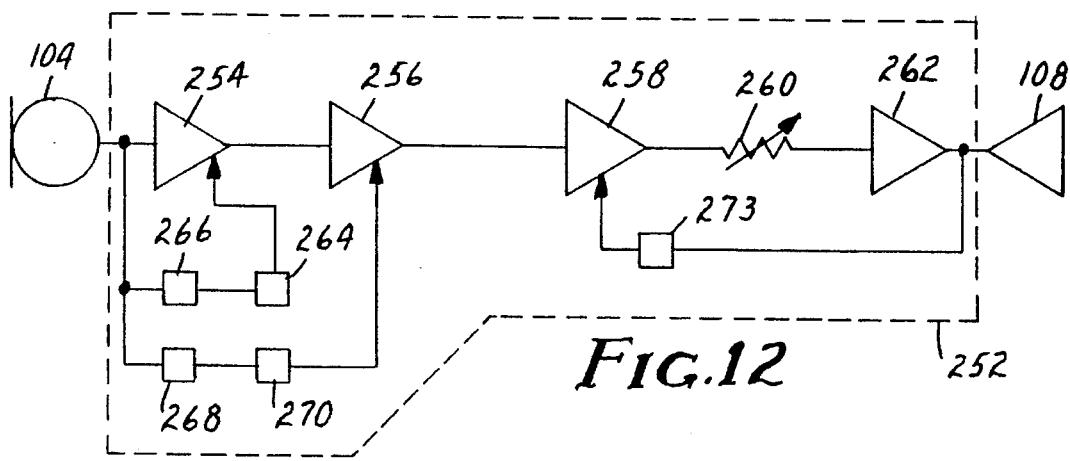

Referring to FIG. 12, adaptive filter 252 includes an adaptive high pass filter 254 and an adaptive low pass filter 256 that together with coupled feedforward loops provide an adaptive bandpass filter. The feedforward loop which controls the adaptive high pass filter 254 includes a low pass filter 266 and cutoff control 264. The feedforward loop which controls the adaptive low pass filter 256 includes a high pass filter 268 and a cutoff control 270. The output from the adaptive band pass filter is fed to an AGC limiter 258, a user adjustable volume control 260, and a power amplifier 262. AGC limiter 258 is controlled by detector 273 which senses the output of power amplifier 262.

Figure 13:
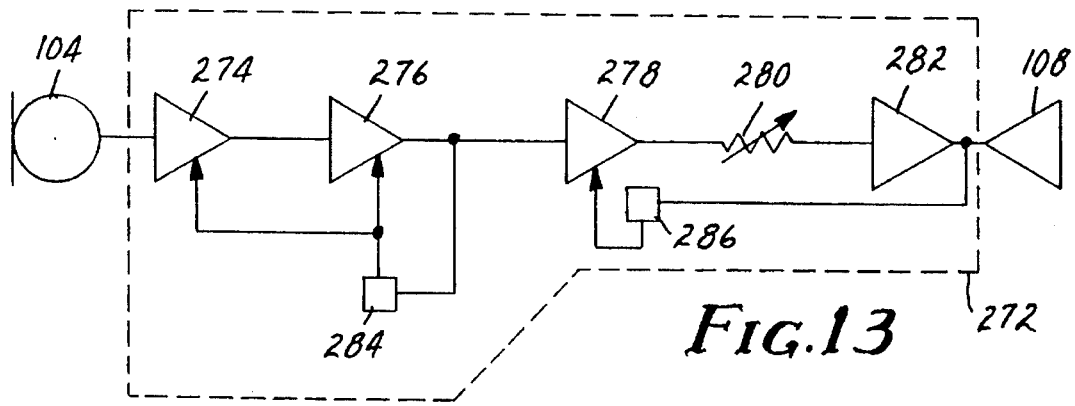

In the circuitry of FIG. 13, adaptive filter 272 includes an adaptive high pass filter 274 and an adaptive low pass filter 276 that together with a coupled feedback loop provides an adaptive bandpass filter. Feedback control of the adaptive high pass filter 274 and the adaptive low pass filter 276 is based on the signal level at the output of the low pass filter 276, the feedback loop includes AC/DC converter 284. Output of the adaptive bandpass filter is fed into an AGC limiter 278, an adjustable volume control 280, and a power amplifier 282. AGC limiter 278 is controlled by detector 286 which senses the output of power amplifier 282.

Figure 14:
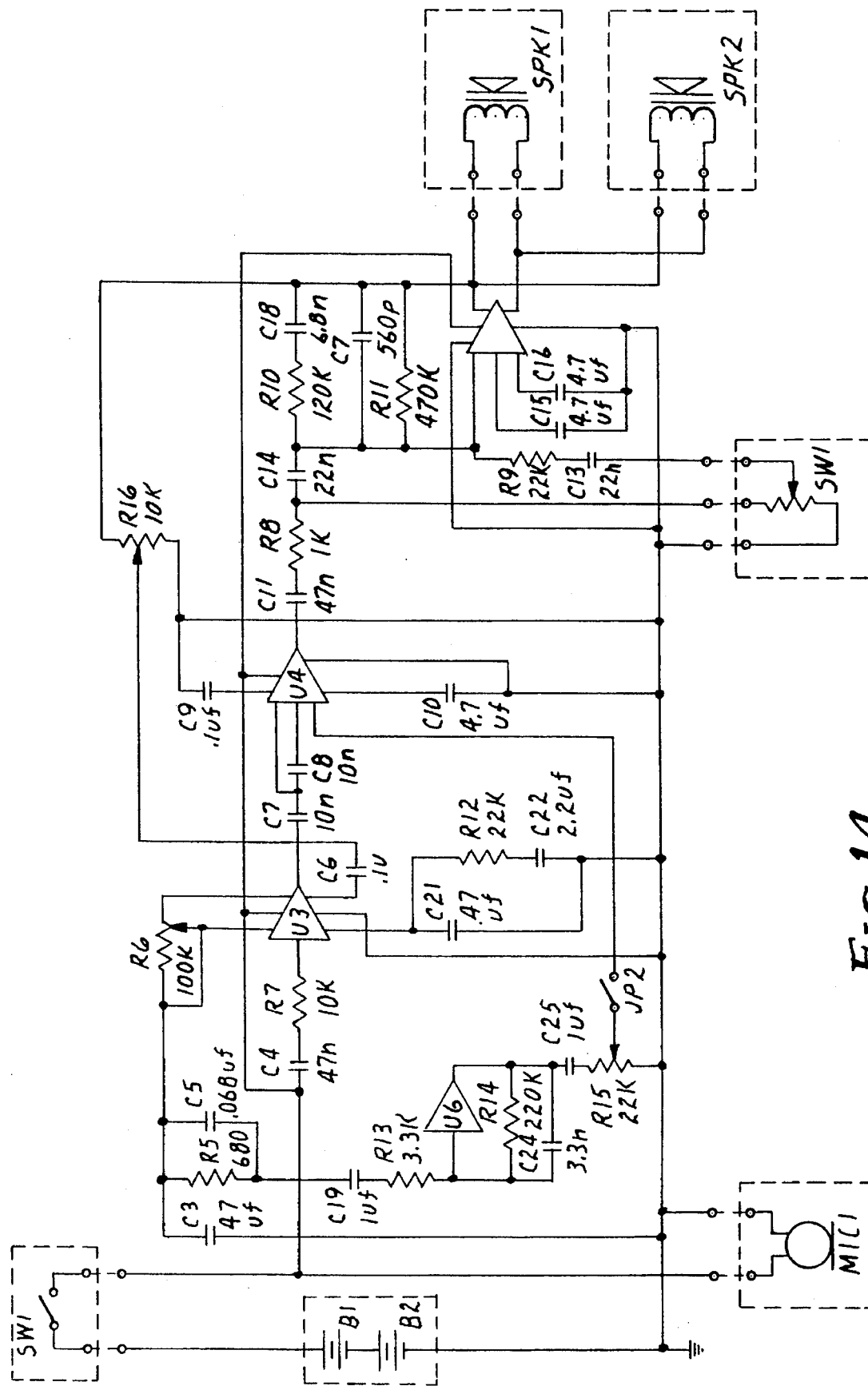
FIG. 14 is an electrical schematic diagram of the present ear device.

FIG. 14 shows a detailed electronic schematic diagram of the ear device shown in FIG. 11. In addition to the circuit components described above with respect to FIG. 5, the circuit of FIG. 14 also includes an adaptive compression circuit including capacitors C20, C21, C22 and resistor R12. The adaptive compression circuit allows the present ear device to adapt not only to varying amplitudes of noise, but also to other characteristics of the background noise in the user's environment. The adaptive compression circuit adapts to these other environmental characteristics to control the response time of the AGC limiter U3. The response time of AGC limiter U3 is defined as the amount of time required for the output of the AGC to react to the input. In certain environments, it is desirable for the output to follow the input very closely. Under other conditions, however, it is desirable for the output to delay following the input for a controlled period of time to prevent a "pumping" effect.

Four sets of time constants control the response time of the AGC limiter U3. The first attack is through C21 and the output impedance of the AC/DC converter in U3, the second attack is through R12/C22. The first release is through C21/R12, and the second release is through C22 and C21 and the input impedance of AGC limiter control input in U3. Preferred time constants are:

| | |
|---|---|
| 1st attack | <1 mS |
| 1st release | 10 mS |
| 2nd attack | 50 mS |
| 2nd release | >1 S |

The short time constants control in the case of single isolated bursts of noise. In that case, the AGC quickly limits the gain applied to the incoming signal in response to the loud burst. In addition, the short release prevents the AGC from limiting the incoming signal to the same extent after the burst of noise is complete. Under these conditions, the short time constants control the response time of the AGC so that the output closely follows the input, thus preventing overcompression of incoming signals following the burst.

The long time constants become active in an environment where noise is more constant or the bursts of noise are very frequent. A printing press room is one example of such an environment. In this environment, the long time constants reduce the overall output of the AGC limiter. The two sets of time constants work together to ensure that the incoming signal is limited appropriately while avoiding an undesirable "pumping" effect.

It shall be understood that the adaptive compression described herein with respect to FIG. 14 could also be used with any of the previously described block diagrams and schematics shown and described with respect to FIGS. 1B, 4, 5, and 10–13, without departing from the spirit and scope of the present invention.

A prototype of the ear protector of FIG. 14 was tested and compared with several commercially available ear protectors. The microphone was adjusted to a string length of 32 mm. The circuit was constructed using the following components:

| | |
|---|---|
| U3 | Gennum Corp. LD502 |
| U4 | Gennum Corp. LF581 |
| U5 | Motorola Corp. MC34119 |
| U6 | Gennum Corp. LC801 |
| Microphone | Panasonic Corp. WM55A103 |
| Speaker | Mouser Corp. 25SP107 |

Two test modes of the present ear device were investigated. In the first test mode, the circuit of FIG. 13 was used. In the second test embodiment, the circuit of FIG. 13 was operated with the switch JP2 in the open position to deactivate the adaptive high pass filter.

The first and second test modes were tested in comparison to the following earmuffs that had been purchased on the open market:

| | Microphone | Type |
|---|---|---|
| "Bilsom" 2390 | omni-dir. | monaural |
| "Bilsom" 2392 | omni-dir. | stereo |
| "Elvex" Com-50 | omni-dir. | monaural |
| "Peltor Tactical" 7 | omni-dir. | stereo |

The "Bilsom" units were available from Bilsom International, Inc., 1100 Sunrise Vally Drive, Reston, Va. 22091.

The "Elvex" unit was available from Elvex Corp., 18 Taylor Avenue, Bethel, Conn. 06801. The "Peltor" unit was available from Peltor AB, Varnamo, Sweden. The quality of construction of each of the comparative earmuffs was at least equal to that of each of the prototypes.

Four volunteer subjects were found to have normal hearing at 500, 1000, 2000 and 4000 HZ, except that the hearing of one was slightly deficient at 500 and 1000 Hz in one ear. Each subject was seated in a sound room that was quiet except when one of two types of recorded noise was presented at a constant level (90 dB SPL) from a source 90 degrees to the left side of the subject, namely 1) of a jackhammer and 2) of pink noise produced by filtering white noise with a single pole low pass filter with a cutoff frequency of 14.5 Hz.

Pre-recorded male voice speech sentences were presented from a source located directly in front of the subject.

The signal-to-noise level of the speech was set to be intelligible in noisy environments at which hearing protection should be provided. Each subject was instructed to turn his/her head and to adjust the level control of the earmuffs until an optimal listening condition was achieved. At a constant noise level, the speech level was lowered until the subject indicated unintelligibility, and the decrease in signal-to-noise ratio for each type of ear muff at this threshold was noted. This was done with the two types of noise, each subject being tested twice for each condition. Throughout the testing, the subject was unaware of the identity of the earmuffs. Mean, normalized test results are reported in Table I.

TABLE I (Threshold of Intelligibility)

| Earmuffs of | Decrease in dB under | |
| --- | --- | --- |
| | Pink noise | Jackhammer |
| First Test Mode | 15 | 13 |
| Second Test Mode | 14 | 14 |
| "Bilsom" 2390 | 11 | 11 |
| "Bilsom" 2392 | 9 | 12 |
| "Elvex" Com-50 | 5 | 7 |
| "Peltor Tactical" 7 | 9 | 12 |

The tests reported in Table I show that the prototype earmuffs enabled the user to understand recorded speech at lower signal-to-noise ratios than did the commercial earmuffs in both the pink noise and jackhammer environments.

Each subject next rated the quality of the speech on a scale of 1 to 10 (1=poorest speech quality) under each noise condition for each of the earmuffs tested. However, the noise level at which each earmuff was tested was set at the threshold of intelligibility for that earmuff. Thus, the signal-to-noise ratio at which the first and second test modes of the present invention was much lower than that for the other earmuffs tested. The subject also judged the quality of the speech in a quiet environment. Mean, normalized test results are reported in Table II.

TABLE II

| Earmuffs | Speech Quality Ratings under | | |
| --- | --- | --- | --- |
| | Quiet | Pink Noise | Jackhammer |
| First Test Mode | 7.0 | 5.8 | 5.1 |
| Second Test Mode | 6.3 | 5.2 | 5.1 |
| "Bilsom" 2390 | 7.1 | 5.5 | 5.5 |
| "Bilsom" 2392 | 6.5 | 5.5 | 5.7 |
| "Elvex" Com-50 | 6.1 | 4.2 | 4.6 |
| "Peltor Tactical" 7 | 7.5 | 6.1 | 5.7 |

The tests reported in Table II show that the prototype earmuffs of each of the first and second test embodiments provided to the user a sound quality substantially equivalent to or better than the other earmuffs tested even though the sound qualities were judged in the noisy environments with lower singal-to-noise ratios than were used when judging the other earmuffs.

As will be understood by those skilled in the art, various combinations of microphones, high and low pass filtering and signal processing can be employed in the present ear device without departing from the spirit and scope of the present invention.

What is claimed is:

1. A device for protecting a user's ears from excessive levels of sound
   while permitting the user to hear desired sounds in a noisy environment, comprising:
   enclosure means for at least partially isolating the user's ears from ambient sounds;
   at least one directional microphone for receiving audio signals; and
   an adaptive band pass filter, connected to receive the audio signals and adapted to output a processed audio signal, the adaptive band pass filter comprising:
   means for sensing the noisiness of the environment and generating therefrom a corresponding control signal;
   an adaptive high pass filter;
   an adaptive low pass filter;
   means responsive to the control signal for automatically adjusting the pass band of the adaptive high pass filter and for automatically adjusting the pass band of the adaptive low pass filter, such that the processed audio signal includes progressively narrower bands of frequencies in progressively noisier environments; and
   an adaptive compression circuit, comprising:
   first time constant means for controlling response time of an automatic gain control circuit in response to isolated bursts of noise; and
   second time constant means for controlling response time of the automatic gain control circuit in response to repetitive bursts of noise.

2. The device according to claim 1 wherein the means for sensing the noisiness further includes means for sensing the amplitude of low frequency noises and generating therefrom a first control signal.

3. The device according to claim 2 wherein the means for sensing the noisiness further includes first cutoff control means for controlling the cutoff frequency of the high pass filter under control of the first control signal.

4. The device according to claim 1 wherein the means for sensing the noisiness further includes means for sensing the amplitude of high frequency noises and generating therefrom a second control signal.

5. The device according to claim 4 wherein the means for sensing the noisiness further includes second cutoff control means for controlling the cutoff frequency of the low pass filter under control of the second control signal.

6. The device according to claim 1 further including detector means, connected to receive the processed signals, for controlling gain provided by the automatic gain control circuit.

7. The device according to claim 1 further including a speaker connected to receive the processed signals.

8. The device according to claim 1 wherein the device comprises a hearing aid.

9. The device according to claim 1 further comprising a second directional microphone.

10. The device according to claim 1 further including an automatic gain control circuit, connected to receive the audio signals, and connected to control the signal level input to the adaptive high pass filter and the adaptive low pass filter.

11. The device according to claim 10 wherein the automatic gain control circuit further equalizes the audio signal over a range of frequencies corresponding to the human voice.

12. The device according to claim 1 further comprising an adjustable volume control.

13. The device according to claim 1 further including means for adjusting the degree of directionality of the microphone.

* * * * *

UNITED STATES PATENT AND TRADEMARK OFFICE
CERTIFICATE OF CORRECTION

PATENT NO.: 5,550,923

DATED: August 27, 1996

INVENTOR(S): David A. Hotvet

It is certified that error appears in the above-identified patent and that said Letters Patent is hereby corrected as shown below:

Column 5, line 62, delete "bind" and insert therefore --band--.

Column 7, line 17, delete "an" and insert therefore --a--.

Signed and Sealed this

Sixteenth Day of December, 1997

*Attest:*

BRUCE LEHMAN

*Attesting Officer*  Commissioner of Patents and Trademarks